United States Patent [19]

Cantatore et al.

[11] Patent Number: 4,906,678
[45] Date of Patent: Mar. 6, 1990

[54] 1,2,2,6,6-PENTAMETHYL-4-PIPERIDYLAMINOTRIAZINE DERIVATIVES AND THEIR USE AS STABILIZERS

[75] Inventors: Giuseppe Cantatore, Bitonto, Italy; Francois Gugumus, Allschwil, Switzerland

[73] Assignee: Ciba-Geigy Corporation, Ardsley, N.Y.

[21] Appl. No.: 264,560

[22] Filed: Oct. 31, 1988

Related U.S. Application Data

[62] Division of Ser. No. 85,581, Aug. 14, 1987, Pat. No. 4,816,507.

[30] Foreign Application Priority Data

Aug. 25, 1986 [IT] Italy ................. 21518 A/86

[51] Int. Cl.⁴ ................. C08K 5/34; C07D 403/12
[52] U.S. Cl. ................. 524/97; 524/98; 540/605; 544/113
[58] Field of Search ................. 524/97, 100, 98; 544/113, 198; 540/605

[56] References Cited

U.S. PATENT DOCUMENTS

4,477,615 10/1984 Raspanti et al. ................. 524/100
4,525,503 6/1985 Cantatore ................. 524/100
4,816,507 3/1989 Cantatore et al. ................. 524/100

*Primary Examiner*—John Kight
*Assistant Examiner*—Kriellion Morgan
*Attorney, Agent, or Firm*—Luther A. R. Hall

[57] ABSTRACT

Compounds of the formula (I)

$$R_1-N(R)-R_2-N(R)-R_3-N(R)-R_4-N(R)-R_5 \quad (I)$$

wherein $R_1$ and $R_5$ are independently hydrogen, $C_1$–$C_{12}$-alkyl, $C_5$–$C_7$-cycloalkyl or a group of the formula (II),

[Structure II: 2,2,6,6-tetramethyl-1-methylpiperidinyl group] (II)

$R_2$, $R_3$ and $R_4$ are independently $C_2$–$C_{12}$-alkylene, R is a group of the formula (III)

[Structure III: triazine group with $R_6$ substituent and pentamethylpiperidinyl] (III)

wherein $R_6$ is $C_2$–$C_8$-dialkylamino, $C_1$–$C_4$-alkoxy, a 5-membered to 7-membered heterocyclic group containing a nitrogen atom which is attached to the triazine residue or a group of the formula (IV),

[Structure IV: pentamethylpiperidinyl-N-$R_8$ group] (IV)

$R_7$ and $R_8$ are independently $C_1$–$C_{12}$-alkyl, $C_5$–$C_7$-cycloalkyl, benzyl or a group of the formula (II), subject to the proviso that both, $R_1$ and $R_5$ are different from hydrogen, if R is a group

[Structure]

are useful as light stabilizers, heat stabilizers and/or oxidation stabilizers for organic materials, in particular synthetic polymers.

15 Claims, No Drawings

1,2,2,6,6-PENTAMETHYL-4-PIPERIDYLAMINO-TRIAZINE DERIVATIVES AND THEIR USE AS STABILIZERS

This is a divisional of application Ser. No. 085,581, filed on Aug. 14, 1987, now U.S. Pat. No. 4,816,507, issued on Mar. 28, 1989.

The present invention relates to novel 1,2,2,6,6-pentamethyl-4-piperidylaminotriazine derivatives which can be used as light stabilizers, heat stabilizers and/or oxidation stabilizers for organic materials, especially synthetic polymers.

It is known that synthetic polymers undergo progressive changes in their physical properties, such as loss of mechanical strength and colour changes, when they are exposed to sunlight or other sources of ultraviolet light.

To retard the deleterious effect of ultraviolet radiation on synthetic polymers, it has been proposed to use various additives having light-stabilizing properties, such as certain benzophenone and benzotriazole derivatives, nickel complexes, alkylidenemalonates, cyanoacrylates and sterically hindered amines.

Japanese Patent Publication Sho No. 57-38589 describes polyalkylpiperidylaminotriazine derivatives and their use as light stabilizers, heat stabilizers and oxidation stabilizers for polymeric materials. In Example 13 of this publication the preparation of $N^I,N^{II},N^{III},N^{IV}$-tetrakis[2,4-bis[N-(1,2,2,6,6-pentamethyl-4-piperidyl)-n-butylamino]-1,3,5-triazin-6-yl]-4,7-diazadecane-1,10-diamine is disclosed. EP 112 690 describes compounds containing three 2,4-bis[pentamethylpiperidylamino]-1,3,5-triazin-6-ylamino radicals and their use as polymer stabilizers.

In Research Disclosure 25, 330 (1985) the compound $N^I,N^{II},N^{III},N^{IV}$-tetrakis[2,4-bis[N-(2,2,6,6-tetramethyl-4-piperidyl)-n-butylamino]-1,3,5-triazin-6-yl]-4,7-diazadecane-1,10-diamine and its use as stabilizer for polyethylene films is disclosed.

The present invention pertains to novel compounds of the formula (I)

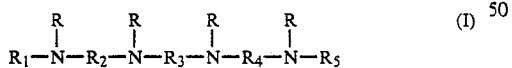

wherein $R_1$ and $R_5$ are independently hydrogen, $C_1$-$C_{12}$-alkyl, $C_5$-$C_7$-cycloalkyl or a group of the formula (II),

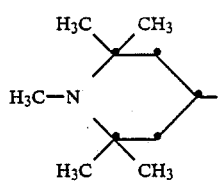

$R_2$, $R_3$ and $R_4$ are independently $C_2$-$C_{12}$-alkylene, R is a group of the formula (III)

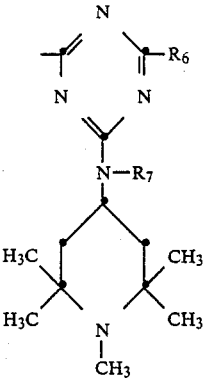

wherein $R_6$ is $C_2$-$C_8$-dialkylamino, $C_1$-$C_4$-alkoxy, a 5-membered to 7-membered heterocyclic group containing a nitrogen atom which is attached to the triazine residue or a group of the formula (IV),

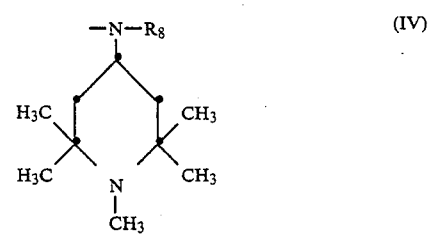

$R_7$ and $R_8$ are independently $C_1$-$C_{12}$-alkyl, $C_5$-$C_7$-cycloalkyl, benzyl or a group of the formula (II), subject to the proviso that both, $R_1$ and $R_5$ are different from hydrogen, if R is a group

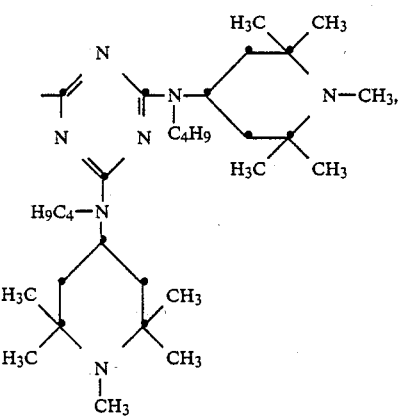

$R_1$, $R_5$, $R_7$ and $R_8$ as $C_1$-$C_{12}$-alkyl are for example methyl, ethyl, propyl, isopropyl, butyl, isobutyl, 2-butyl, t-butyl, pentyl, isopentyl, hexyl, heptyl, 3-heptyl, octyl, 2-ethylhexyl, nonyl, decyl, undecyl or dodecyl. $C_1$-$C_6$-alkyl which may be straight chain or branched is preferred. $R_1$ and $R_5$ are preferably methyl and $R_7$ and $R_8$ are preferably methyl, ethyl or butyl, in particular n-butyl.

$R_1$, $R_5$, $R_7$ and $R_8$ as $C_5$-$C_7$-cycloalkyl are for example cyclopentyl, cyclohexyl or cycloheptyl, preferably cyclohexyl.

$R_2$, $R_3$ and $R_4$ as $C_2$-$C_{12}$-alkylene are for example ethylene, trimethylene, tetramethylene, pentamethylene, 2,2-dimethyltrimethylene, hexamethylene, trimethylhexamethylene, decamethylene or dodecamethylene. $C_2$–$C_6$-alkylene is preferred. $R_2$ and $R_4$ as trimethylene and $R_3$ as ethylene are particularly preferred.

$R_6$ as $C_2$–$C_8$-dialkylamino is for example dimethylamino, diethylamino, dipropylamino, diisopropylamino, dibutylamino or diisobutylamino.

$R_6$ as $C_1$–$C_4$-alkoxy is for example methoxy, ethoxy, propoxy, isopropoxy, butoxy or isobutoxy.

$R_6$ as a 5-membered to 7-membered heterocyclic group containing a nitrogen atom which is attached to the triazine residue is for example pyrrolidinyl, piperidino, morpholino or hexahydroazepinyl, in particular morpholino.

Those compounds of formula (I) are preferred, wherein $R_6$ is $C_2$–$C_8$-dialkylamino, morpholino or a group of the formula (IV).

Those compounds of formula (I) are particularly preferred, wherein $R_6$ is a group of the formula (IV) and $R_7$ and $R_8$ are independently $C_1$–$C_{12}$-alkyl or a group of the formula (II).

$R_1$ and $R_5$ are preferably $C_1$–$C_{12}$-cycloalkyl or a group of the formula (II), in particular $C_1$–$C_6$-alkyl or a group of the formula (II).

Compounds of formula (I) wherein $R_1$ and $R_5$ are methyl, $R_2$, $R_3$ and $R_4$ are independently ethylene or trimethylene, $R_6$ is a group of the formula (IV) and $R_7$ $R_8$ are independently $C_1$–$C_4$-alkyl or a group of the formula (II), are also preferred.

Those compounds of formula (I) are of interest, wherein $R_1$ and $R_5$ are methyl, $R_2$ and $R_4$ are trimethylene, $R_3$ is ethylene, $R_6$ is a group of the formula (IV), $R_7$ and $R_8$ which are identical are $C_1$–$C_{12}$-alkyl.

$R_7$ and $R_8$ are preferably $C_1$–$C_6$-alkyl, in particular methyl, ethyl or butyl, and especially preferred n-butyl.

The compounds of the formula (I) can be prepared by various methods known per se, for example by N-methylation of compounds of the formula (Ia)

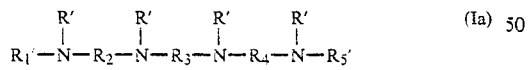  (Ia)

wherein $R_1'$ and $R_5'$ are independently hydrogen, $C_1$–$C_{12}$-alkyl, $C_5$–$C_7$-cycloalkyl or a group of the formula (II'),

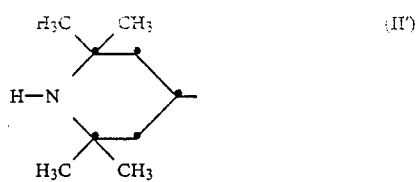  (II')

$R_2$, $R_3$ and $R_4$ have the meanings given above, $R'$ is a group of the formula (III'),

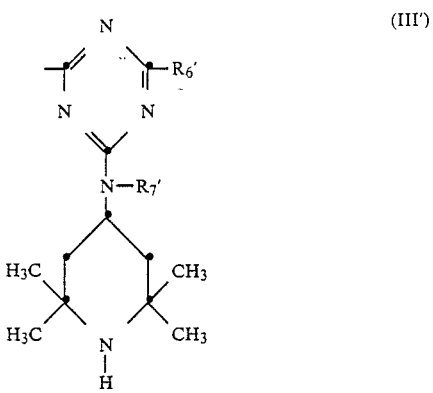  (III')

$R_6'$ is $C_2$–$C_8$-dialkylamino, $C_1$–$C_4$-alkoxy, a 5-membered to 7-membered heterocyclic group containing a nitrogen atom which is attached to the triazine residue or a group of the formula (IV'),

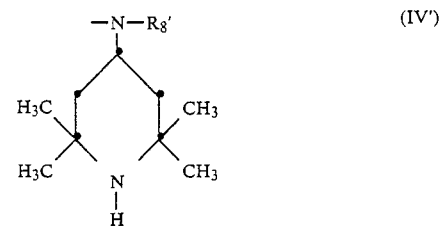  (IV')

$R_7'$ and $R_8'$ are independently $C_1$–$C_{12}$-alkyl, $C_5$–$C_7$-cycloalkyl, benzyl or a group of the formula (II').

The N-methylation can be carried out by various methods known per se, for example by reacting the compound of the formula (Ia) with an excess of formaldehyde and formic acid (Eschweiler-Clarke reaction) or with formaldehyde and hydrogen in the presence of an hydrogenation catalyst such as e.g. platinum or palladium.

If $R_1'$ are hydrogen, it is possible that none or only one of these hydrogens is exchanged by a methyl group during the N-methylation of the compounds of formula (Ia). This depends on the reaction conditions, for example the reaction time and the molar amount of formaldehyde and formic acid used.

Accordingly the reaction mixture may still contain amounts of compounds of the formulae (Ib) and (Ic)

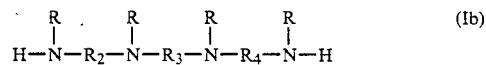  (Ib)

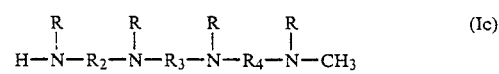  (Ic)

wherein R, $R_2$, $R_3$ and $R_4$ are as defined above. Such reaction mixtures can be used in the same way as the pure final product as long as the content of the incompletely methylated compounds of the formulae (Ib) and (Ic) does not exceed 30%.

If desired, the compounds of the reaction mixture can be separated in a conventional manner, for example by chromatographic methods.

A further preferred embodiment of the invention is a composition comprising 70% to 99% by weight of a compound of the formula (I) wherein $R_1$ and $R_5$ are methyl, R, $R_2$, $R_3$ and $R_4$ have the meanings given above and 0 to 30% by weight of a compound of the formula (Ib)

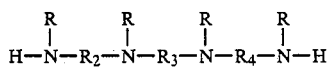

and 0 to 30% by weight of a compound of the formula (Ic),

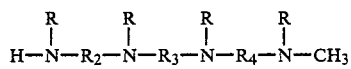

wherein R, $R_2$, $R_3$ and $R_4$ are as defined above.

A composition comprising 70% to 99% by weight of a compound of formula (I) wherein $R_1$ and $R_5$ are methyl, $R_2$ and $R_4$ are trimethylene, $R_3$ is ethylene, R is a group of the formula (III) wherein $R_6$ is a group of the formula (IV) and $R_7$ and $R_8$ which are identical are $C_1$-$C_{12}$-alkyl and 0 to 30% by weight of a compound of the formula (Ib) and 0 to 30% by weight of a compound of the formula (Ic) wherein R, $R_2$, $R_3$ and $R_4$ are as defined above, is especially preferred.

The compounds of the formula (Ia) can be prepared by analogy to known processes, for example as described in U.S. Pat. No. 4,108,829. Preferably, they are prepared by reacting a polyamine of the formula

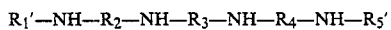

with a triazine of the formula

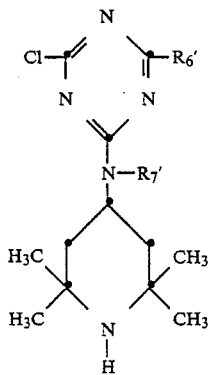

$R_1'$, $R_2$, $R_3$, $R_4$, $R_5'$, $R_6'$ and $R_7'$ are as defined above.

The reaction can be carried out in an inert solvent in the presence of a base, preferably an inorganic base, in a quantity at least equivalent to the hydrochloric acid liberated in the reaction.

The starting materials are known or can be prepared by analogy to known methods.

The compounds of formula (I) are very effective in improving the light stability, heat stability and/or oxidation stability of organic materials, in particular synthetic polymers, especially polyolefins.

In general polymers which can be stabilized include:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefines and diolefines with each other or with other vinyl monomers, such as, for example, ethylene/propylene, linear low density polyethylene (LLDPE) and its mixtures with low density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in 1) above, for example polypropylene/ethylene-propylene-copolymers, LDPE/EVA, LDPE/EAA, LLDPE/EVA and LLDPE/EAA.

3a. Hydrocarbon resins (for example $C_5$-$C_9$) and hydrogenated modifications thereof (for example tackyfiers).

4. Polystyrene, poly-(p-methylstyrene), poly-α-methylstyrene).

5. Copolymers of styrene or α-methylstyrene with dienes or acrylic derivatives, such as, for example, styrene/butadiene, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadien, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylenediamine and adipic acid; polyamides prepared from hexamethylene diamine and isophthalic or/and terephthalic acid and optionally an elastomer as modifier, for example poly-2,4,4,-trimethylhexamethylene terephthalamide or poly-m-phenylene isophthalamide. Further copolymers of the aforementioned polyamides with polyolefins, olefin copolymers, ionomers or chemically bonded or grafted elastomers; or with polyethers, as for instance, with polyethylene glycol, polypropylene glycol or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2,-(4-hydroxyphenyl)-propane] terephthalate and polyhydroxybenzoates as well as block-copolyether-esters derived from polyethers having hydroxyl end groups.

18. Polycarbonates and polyester-carbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyesteracrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose; rosins and their derivatives.

27. Mixtures of polymers as mentioned above, for example PP/EPDM, Polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

The compounds of fomula (I) are especially useful as stabilizers for non-crosslinked homo- or copolymers of α-olefins containing at least 80% of polymerized α-olefin, in particular homopolymers of ethylene, propylene, 1-butene, 2-methylpropene, 3-methyl-1-butene or 4-methyl-1-pentene and their copolymers with each other or with other unsaturated compounds such as styrene, butadiene, vinyl acetate, acrylic acid, methyl or ethyl acrylate or methyl or ethyl methacrylate. Of particular technical interest are polyethylene and polypropylene.

The compounds of formula (I) can be mixed with the organic material in various proportions depending on the nature of the material to be stabilized, on the end use and on the presence of other additives.

In general it is advantageous to employ from 0.01 to 5% by weight of the compounds of formula (I), relative to the weight of the material to be stabilized, preferably from 0.1 to 2%.

The compounds of formula (I) can be incorporated into the organic material via various processes known per se, such as e.g. dry blending in the form of powders, or wet mixing in the form of solutions or suspensions, or mixing in the form of a master-batch which contains the compounds of formula (I) in a concentration of e.g. 5 to 25% by weight; in these operations, the organic material can be employed in the form of powder, granules, a solution, a suspension or in the form of a latex.

The compounds of formula (I) and, if desired, further additives can also be mixed into a melt of the material to be stabilized, before or during shaping.

The resulting stabilized materials can be applied in various forms, e.g. sheets, fibres, tapes, bottles, tubes or other profiles. The compounds of formula (I) are especially useful as stabilizers for polypropylene fibres, tapes and films.

If desired, other additives, such as e.g. antioxidants, phosphites, UV absorbers, nickel stabilizers, pigments, fillers, plasticizers, antistatic agents, blowing agents, flameproofing agents, lubricants, anti-corrosion agents and metal deactivators, can be added to the mixture of the compounds of the invention with the organic materials. Examples of additives which can be mixed with the compounds of formula (I) are in particular:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis-[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate.

1.6. Acylaminophenols, for example 4-hydroxyanilide of lauric acid, 4-hydroxyanilide of stearic acid, 2,4-bis(octylmercapto)-6-(3,5-di-tert-butyl-4-hydroxyanilino)-s-triazine, octyl N-(3,5-di-tert-butyl-4-hydroxyphenyl)carbamate.

1.7. Esters of $\beta$-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.8. Esters of $\beta$-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.9. Esters of $\beta$-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.10. Amides of $\beta$-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylene-diamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis($\alpha,\alpha$-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives. 2.3. Esters of substituted and unsubstituted benzoic acids, for example, 4-tert-butylphenyl salicylate, phenyl salicylate, octylphenyl salicylate, dibenzoylresorcinol, bis(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl $\alpha$-cyano-$\beta,\beta$-diphenylacrylate, isooctyl $\alpha$-cyano-$\beta,\beta$-diphenylacrylate, methyl $\alpha$-carbomethoxycinnamate, methyl $\alpha$-cyano-$\beta$-methyl-p-methoxycinnamate, butyl $\alpha$-cyano-$\beta$-methyl-p-methoxycinnamate, methyl $\alpha$-carbomethoxy-p-methoxycinnamate and N-($\beta$-carbomethoxy-$\beta$-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or with out additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoneoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane tetracarboxylate, 1,1'-(1,2-ethanediyl)bis(3,3,5,5-tetramethylpiperazinone).

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic acid dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearyl pentaerythritol -diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylene diphosphonite, 3,9-bis(2,4-di-tert-butylphenoxy)-2,4,8,10-tetraoxa-3,9-diphosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

The compounds of formula (I) are particularly effective in combination with phenolic antioxidants, preferably those mentioned above under items 1.1 to 1.10. The antioxidant may be added in an amount of e.g. 0.01 to 0.5% by weight, relative to the weight of the organic material.

The following examples illustrate the invention.

EXAMPLE 1:

Preparation of $N^I,N^{II},N^{III},N^{IV}$-tetrakis[2,4-bis[N-1,2,2,6,6-pentamethyl-4-piperidyl)-n-butylamino]-1,3,5-triazin-6-yl]-$N^I,N^{IV}$-dimethyl-4,7-diazadecane-1,10-diamine To a solution of 43.4 g (0.02 moles) of $N^I,N^{II},N^{III},N^{IV}$-tetrakis-[2,4-bis[N-(2,2,6,6-tetramethyl-4-piperidyl)-n-butylamino]-1,3,5-triazin-6-yl]-4,7-diazadecane-1,10-diamine in 100 ml of water containing 18.4 g (0.4 moles) of formic acid there are added 30 ml (0.4 moles) of a 40% aqueous formaldehyde solution during about 30 minutes.

The solution is heated under reflux for 8 hours. After cooling to room temperature an additional amount of 15 ml of 40% formaldehyde is added and the solution refluxed for additional 5 hours.

After cooling a solution of 20 g (0.5 moles) of NaOH in 100 ml water is added. The precipitated solid is filtered off, washed with water, dried under vacuum and recrystallized from isopropanol. The obtained title compound melts at 154°–160° C.

| Analysis for $C_{134}H_{254}N_{32}$ (Molecular weight: 2313.7 g/mol): | | | |
|---|---|---|---|
| calculated | C = 69.56%; | H = 11.06%; | N = 19.37% |
| found | C = 69.36%; | H = 10.98%; | N = 19.25% |

EXAMPLES 2 TO 6:

In analogy to the procedure described in Example 1 the following compounds are prepared:

$$\underset{|}{\overset{R}{N}}-\text{CH}_3 \quad \text{H}_3\text{C}-\underset{|}{\overset{R}{N}}-(\text{CH}_2)_3-\underset{|}{\overset{R}{N}}-(\text{CH}_2)_2-\underset{|}{\overset{R}{N}}-(\text{CH}_2)_3-\underset{|}{\overset{R}{N}}-\text{CH}_3$$

R =

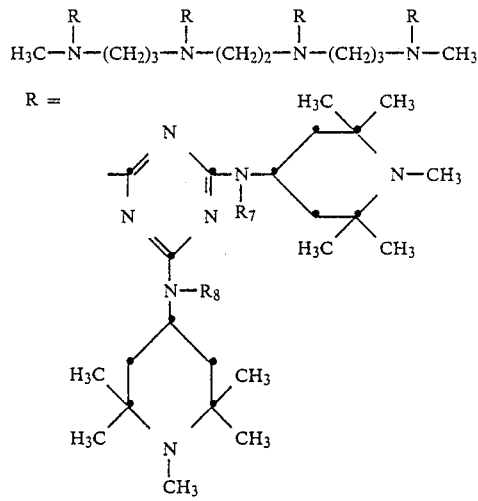

| Example No. | $R_7/R_8$ | Melting point (°C.) |
|---|---|---|
| 2 | —CH₃ | 208–214 |
| 3 | —C₂H₅ | 197–201 |
| 4 | —C₃H₇—i | 211–216 |
| 5 | —CH—C₂H₅<br>\|<br>CH₃ | 186–190 |

-continued

| Example No. | R7/R8 | Melting point (°C.) |
|---|---|---|
| 6 | 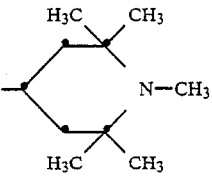 | 247–252 |

EXAMPLE 7:

Preparation of N$^I$,N$^{II}$,N$^{III}$,N$^{IV}$-tetrakis[2,4-bis[N-1,2,2,6,6-pentamethyl-4-piperidyl)-n-butylamino]-1,3,5-triazin-6-yl]-N$^I$,-N$^{IV}$-dimethyl-3,6-diazaoctane-1,8-diamine This compound is prepared by analogy to the procedure described in Example 1.

The melting point of the product is 151°–155° C.

EXAMPLE 8:

Light stability of polypropylene tapes

100 Parts of polypropylene powder (melt flow index: ~1.5 g/10 min; measured at 230° C. and 2.16 kg) are blended in a barrel mixer with 0.05 parts of pentaerythrityl-tetrakis(β-3,5-di-tert-butyl-4-hydroxyphenyl)-propionate, 0.05 parts of tris(2,4-di-tert-butylphenyl)-phosphite, 0.1 part of Ca-stearate and 0.1 part of the product of Example 1 (=LS 1). Then the blend is compounded in an extruder at temperatures of 180°–220° C. The granules obtained on extrusion and granulation are transformed into films at 220°–260° C. in a second extruder equipped with a flat sheet die. The films are cut into ribbons which are drawn to achieve a stretch ratio of 1:6. The tapes obtained with this procedure are finally 50 μm thick and 2.5 mm wide.

The tapes are mounted without tension on sample holders and exposed in a Xenotest 1200. Periodically, the tensile strength of the exposed tapes is measured. The exposure time corresponding to a loss of 50% of the initial tensile strength (T$_{50}$) is a measure for the light-stabilizing efficiency. In the case of the stabilized sample T$_{50}$ is 3400 hours. A comparative sample without LS 1 shows a T$_{50}$ of 680 hours.

EXAMPLE 9:

Oven aging of polypropylene

In the mixing chamber of a Brabender plastograph 38 g of unstabilized polypropylene powder (melt flow index: ~3 g/10 min; measured at 230° C. and 2.16 kg) are plasticized and homogenized with 38 mg of Ca-stearate and the stabilizers indicated in table 1 at 200° C. and 30 rpm for 10 minutes. The homogenized mixture is then taken out of the kneader and compression molded at 260° C. for 6 minutes into a 1 mm thick sheet which is cut into test specimens of 1×13 cm$^2$.

The test specimens are placed in draft air ovens at 135° C. and checked periodically for brittleness on bending.

The test results are summarized in table 1.

TABLE 1

| Stabilizer (% by weight) | Days at 135° C. until brittleness on bending |
|---|---|
| none | <1 |
| 0.2% LS 1 | 1 |
| 0.2% AO 1 | 54 |
| 0.1% LS 1 + 0.1% AO 1 | 84 |

LS 1 = Product of Example 1
AO 1 = Octadecyl β-(3,5-di-tert-butyl-4-hydroxyphenyl)propionate

EXAMPLE 10:

1 g of each of the compounds indicated in table 2 and 1 g of calcium stearate are mixed in a powder mixer with 1000 g of polypropylene powder (melt index: 2 g/10 min; measured at 230° C. and 2.16 kg). The mixtures are extruded twice at 200° to 220° C. to give polymer granules which are then converted into 1 mm thick sheets (mould in accordance with DIN 53 451) by compression-injection for 3 minutes at 220° C. The sheets obtained are exposed in a draft air oven at 135° C. and checked periodically for brittleness on bending at 180°.

The results are shown in table 2:

TABLE 2

| Stabilizer | Hours at 135° C. until brittleness on bending at 180° |
|---|---|
| without | 330 |
| Compound of Example 1 | 1320 |
| Compound of Example 2 | 1800 |
| Compound of Example 3 | 1580 |

We claim:

1. A compound of the formula (I)

wherein R$_1$ and R$_5$ are independently hydrogen, C$_1$–C$_{12}$-alkyl, C$_5$–C$_7$-cycloalkyl or a group of the formula (II),

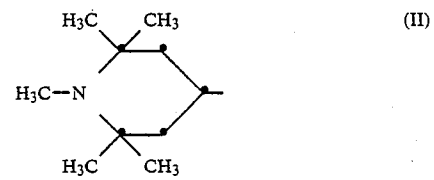

R$_2$, R$_3$ and R$_4$ are independently C$_2$–C$_{12}$-alkylene, R is a group of the formula (III)

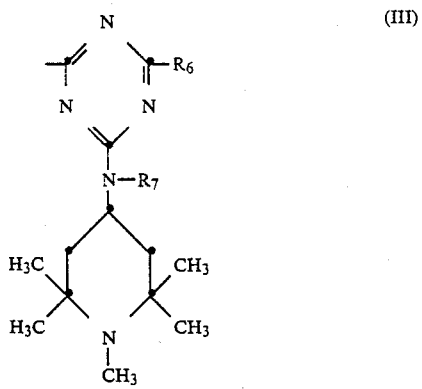

wherein $R_6$ is morpholino or hexahydroazepinyl and $R_7$ is $C_1$–$C_{12}$-alkyl, $C_5$–$C_7$-cycloalkyl, benzyl or a group of the formula (II).

2. The compound according to claim 1, wherein $R_6$ is morpholino.

3. The compound according to claim 1, wherein $C_1$–$C_{12}$-alkyl or a group of the formula (II).

4. The compound according to claim 1, wherein $R_1$ and $R_5$ are independently $C_1$–$C_{12}$-alkyl, $C_5$–$C_7$-cycloalkyl or a group of the formula (II).

5. The compound according to claim 1, wherein $R_1$ and $R_5$ are independently $C_1$–$C_6$-alkyl or a group of the formula (II).

6. The compound according to claim 1, wherein $R_1$ and $R_5$ are methyl, $R_2$, $R_3$ and $R_4$ are independently ethylene or trimethylene, and $R_7$ is $C_1$–$C_4$-alkyl or a group of the formula (II).

7. The compound according to claim 1, wherein $R_1$ and $R_5$ are methyl, $R_2$ and $R_4$ are trimethylene, $R_3$ is ethylene, $R_7$ is $C_1$–$C_{12}$-alkyl.

8. The compound according to claim 1, wherein $R_7$ is $C_1$–$C_6$-alkyl.

9. The compound according to claim 1, wherein $R_7$ is methyl, ethyl or butyl.

10. The compound according to claim 1, wherein $R_7$ is n-butyl.

11. A composition stabilized against light oxidation or heat induced degradation which comprises
   (a) a polymer, and
   (b) an effective stabilizing amount of at least one compound according to claim 1.

12. A composition according to claim 11, wherein the polymer is polyethylene or polypropylene.

13. A composition according to claim 11, which additionally contains a phenolic antioxidant.

14. A composition comprising 70% to 99% by weight of a compound according to claim 1, wherein $R_1$ and $R_5$ are methyl, and 0 to 30% by weight of a compound of the formula (Ib)

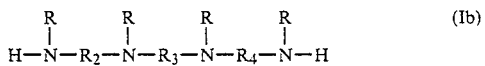

and 0 to 30% by weight of a compound of the formula (Ic)

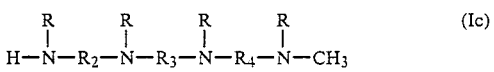

wherein R, $R_2$, $R_3$ and $R_4$ are as defined in claim 1, and wherein at least one compound of formula Ib or Ic must be present.

15. A method for stabilizing a polymer against oxidative, thermal or light induced degradation which comprises incorporating into said polymer an effective stabilizing amount of at least one compound according to claim 1.

* * * * *